United States Patent
Huo

(10) Patent No.: US 7,517,984 B2
(45) Date of Patent: Apr. 14, 2009

(54) MANUFACTURING PROCESS FOR FACIAL TRIS-CYCLOMETALLATED COMPLEXES

(75) Inventor: Shouquan Huo, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 568 days.

(21) Appl. No.: 11/240,288

(22) Filed: Sep. 30, 2005

(65) Prior Publication Data
US 2007/0078264 A1 Apr. 5, 2007

(51) Int. Cl.
*C07F 15/00* (2006.01)
(52) U.S. Cl. .......................................... 546/4
(58) Field of Classification Search .................. None
See application file for complete search history.

(56) References Cited

U.S. PATENT DOCUMENTS 6,835,835 B1 12/2004 Huo

FOREIGN PATENT DOCUMENTS

JP 2004-189673 7/2004

OTHER PUBLICATIONS

S. Huo, "Facial Tris-Cyclometallated Group 9 Complex Synthesis", U.S. Appl. No. 11/015,910, filed Dec. 17, 2004.
S. Huo, "Isomerization of Tris-Cyclometallated Iridium Complexes", U.S. Appl. No. 11/134,120, filed May 20, 2005.
A. B. Tamayo, et al., "Synthesis and Characterization of Facial and Meridional Tris-Cyclometalated Iridium (III) Complexes", J. Am. Chem. Soc., 2003, 125, pp. 7377-7387.
Probing the mer-to fac-Isomerization of Tris-Cyclometallated Homo- and Heteroleptic $(C_2N)_3$ Iridium (III) Complexes, Inorganic Chemistry, 2008, 47, 6681-6691, Aidan R. Mcdonald, et al.

*Primary Examiner*—Zinna N Davis
(74) *Attorney, Agent, or Firm*—Arthur E. Kluegel; Raymond L. Owens

(57) ABSTRACT

A process for forming a facial tris-cyclometallated iridium or rhodium complex isomer comprises heating an original composition containing (a) a meridional isomer of a tris-cyclometallated iridium or rhodium complex in (b) an organic hydrocarbon solvent, a halogenated hydrocarbon solvent, or a combination thereof, to a reaction temperature of least 150° C. for a time sufficient to form a product containing the facial isomer in an increased ratio to meridional isomer compared to the original composition. The process is simple and efficient and provides improved purity.

22 Claims, No Drawings

MANUFACTURING PROCESS FOR FACIAL TRIS-CYCLOMETALLATED COMPLEXES

BACKGROUND OF THE INVENTION

Cyclometallated iridium complexes have been the focus of research and development in OLED (Mark E. Thompson et al, WO 01/41512 A1) display devices over last several years. Those complexes can offer higher efficiency when used as phosphorescent dopants in OLED devices since both singlet and triplet excitons generated by electroexcitation can be harvested by a phosphorescent dopant, while only singlets (25% of total excitons) can be utilized when a fluorescent material is used as a dopant. Tris-cyclometallated iridium complexes have demonstrated such advantage. There exist two stereoisomers in homoleptic tris-cyclometallated iridium complexes such as tris(2-(phenyl)pyridinato-$N,C^2$)iridium (III)(Ir(ppy)$_3$), namely facial and meridional isomers as shown below. The facial isomer has been shown to be more desirable as it has demonstrated higher quantum yield and thermal stability than the corresponding meridional isomer (A. B. Tamayo, et al, *J. Am. Chem. Soc.* 2003, 125, 7377).

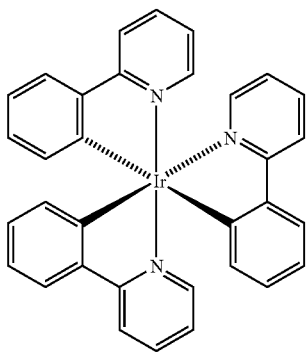

meridional Ir(ppy)$_3$

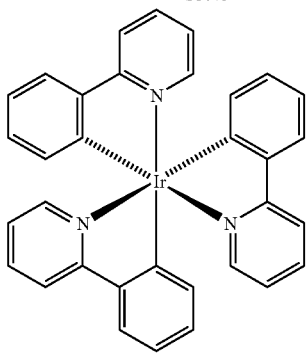

facial Ir(ppy)$_3$

There are continuing efforts to develop new phosphorescent dopants for improving the efficiency and operational stability of OLED devices. Heteroleptic (mixed) tris-cyclometallated iridium complexes have recently attracted attention of research community and their applications to OLED devices have been demonstrated (T. Igarashi et al, US 2001/0019782 A1; J. Kamatani, et al, US 2003/0068526 A1; S. Akiyama et al, JP2003-192691A). However, the synthesis of those heteroleptic complexes is challenging. The method employed in the prior arts involves the reaction of a bis-cyclometallated iridium complex with a third ligand in glycerol at high temperature (usually above 180° C.), which we found to produce a mixture of different homoleptic and heteroleptic tris-cyclometallated iridium complexes formed from ligand-scrambling side reactions and lead to difficulties in separation and purification of desired compounds. Recently, we have developed a novel method to prepare mixed tris-cyclometallated iridium complexes in high yields and purity, but the products obtained from this reaction are meridional isomers (S. Huo, U.S. Pat. No. 6,835,835). We also discovered that some meridional isomers could isomerize to their facial isomers by heating the meridional isomer in DMSO, but it was accompanied by severe decomposition in some cases. Another method for this isomerization involves the use of an acid and silica gel particles (U.S. Ser. No. 11/015,910 filed Dec. 17, 2004). Although the method allowed isolation of pure facial isomer readily, the yield of the product was not satisfactory. Recently, we also reported a solid-state isomerization process (U.S. Ser. No. 11/134,120 filed May 20, 2005).

Thompson et al reported thermal (by refluxing the meridional isomer in glycerol) or photochemical isomerization of homoleptic meridional tris-cyclometallated iridium complexes (Tamayo et al, *J. Am. Chem. Soc.* 2003, 125, 7377-7387). A similar photochemical isomerization of homoleptic tris-cyclometallated iridium complexes from meridional isomers to facial isomers is also disclosed in a patent application (JP 2004189673 A2). However, we found that the methods did not work for some heteroleptic tris-cyclometallated iridium complexes such as meridional bis-(1-phenylisoquinolinato-$C^2$,N)(phenylpyridinato-$C^2$,N)iridium(mer-Ir(1-piq)$_2$ (ppy)). For example, thermal isomerization of mer-Ir(1-piq)$_2$(ppy) in glycerol under the same conditions described in the literature (Tamayo et al, *J. Am. Chem. Soc.,* 2003, 125, 7377-7387) resulted in largely decompositions and severe ligand-scrambling. Photo irradiation of mer-Ir(1-piq)$_2$(ppy) did not produce the corresponding facial isomer. Moreover, the photochemical process may not be suitable for large-scale productions and the use of glycerol is not convenient for isolation and purification of the product.

It is a problem to be solved to provide a simple and efficient process for the isomerization of meridional tris-cyclometallated iridium complexes to their facial isomers.

SUMMARY OF THE INVENTION

The invention provides a process for forming a facial tris-cyclometallated iridium or rhodium complex isomer comprising heating an original composition containing (a) a meridional isomer of a tris-cyclometallated iridium or rhodium complex in (b) an organic hydrocarbon solvent, a halogenated hydrocarbon solvent, or a combination thereof, to a reaction temperature of least 150° C. for a time sufficient to form a product containing the facial isomer in an increased ratio to meridional isomer compared to the original composition. The process is simple and efficient and provides improved purity.

DETAILED DESCRIPTION OF THE INVENTION

The invention is generally summarized above.

Tris-cyclometallated complexes related to the invention can be either homoleptic or heteroleptic complexes and may be represented by one of the following formulas:

$$ML_3 \qquad (1)$$

$$M(L')_2L'' \qquad (2)$$

$$ML'L''L''' \qquad (3)$$

wherein M is the metal Ir or Rh, L, L', L", and L''' are monoanionic bidentate ligands that can be coordinated to M through a carbon and a heteroatom donor. Suitably, L, L', L", and L''' represent the ligand that can be coordinated to M through carbon and nitrogen donors. Conveniently, the ligand can be derived from phenylpyridine, phenylisoquinoline, phenylquinoline, phenylpyrimidine, and their derivatives and analogues.

The invention particularly relates to a process for forming a facial tris-cyclometallated iridium or rhodium complex isomer, of formula $M(piq)_2(ppy)$ and $M(piq)_2(ppy)$, from the meridional isomer, comprising subjecting a composition containing the meridional isomer to a thermal isomerization reaction in an organic hydrocarbon solvent or a halogenated hydrocarbon solvent, wherein piq is a 1-phenylisoquinoline, or 3-phenylisoquinoline group, and piq is a 2-phenylquinoline group; and ppy is a 2-phenylpyridine group as represented by Equation 1:

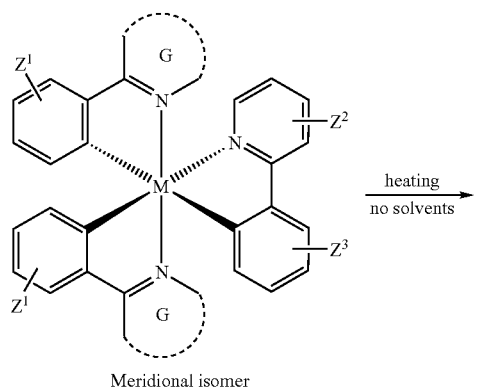

(1)

wherein,

M represents Ir or Rh, preferably Ir,

G represents an isoquinoline or quinoline group, and $Z^1$, $Z^2$, and $Z^3$ represent hydrogen or one or more independently selected groups.

The facial isomer is defined as the stereoisomer of a tris-cyclometallated iridium complex wherein three monoanionic bidentate ligands coordinate to the metal with a facial arrangement of the three heteroatom donors and a facial arrangement of the three carbon donors. Similarly, the meridional isomer has a meridional arrangement of the three heteroatom donors and a meridional arrangement of the three carbon donors. As mentioned before, there exist two stereoisomers in homoleptic tris-cyclometallated iridium complexes where three ligands are the same, namely a facial and a meridional isomer. However, when three ligands that coordinate to the iridium are different from each other or two are the same and the third one is different, a heteroleptic tris-cyclometallated iridium complex is formed and the total number of meridional and facial isomers of this compound may be more than two. Examples of mer- and fac-isomers of heteroleptic tris-cyclometallated iridium complex $Ir(1-piq)_2(ppy)$ are shown below:

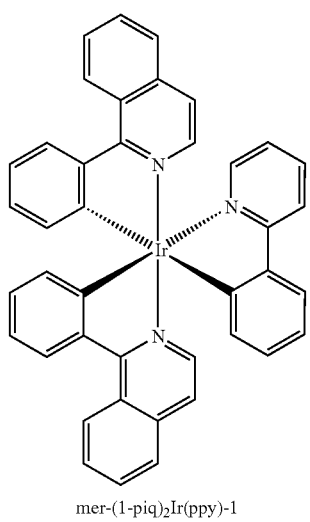

mer-(1-piq)$_2$Ir(ppy)-1

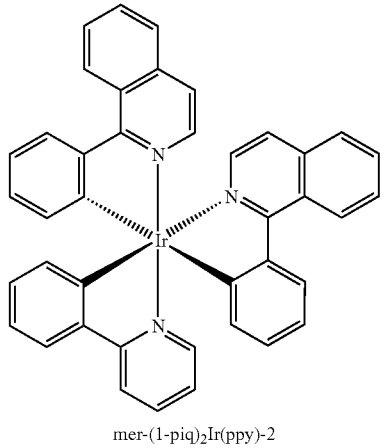

mer-(1-piq)$_2$Ir(ppy)-2

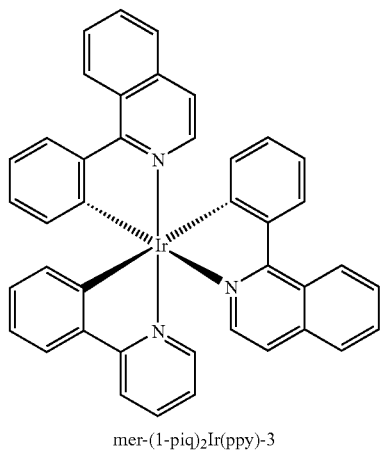

mer-(1-piq)$_2$Ir(ppy)-3

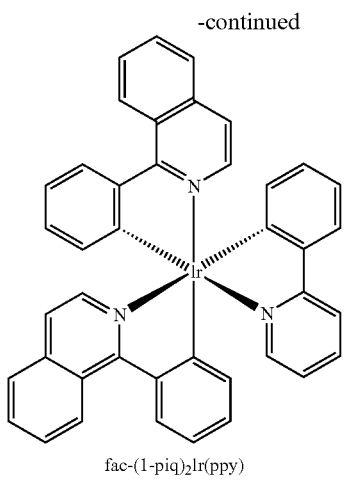

fac-(1-piq)₂Ir(ppy)

The piq ligand can be a 1-phenylisoquinoline or a 3-phenylisoquinoline group, and pq is a 2-phenylquinoline group as represented by the following formulas,

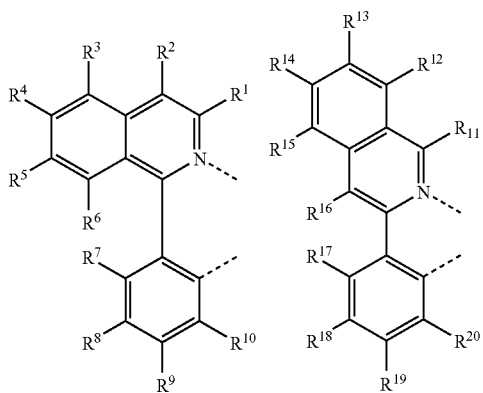

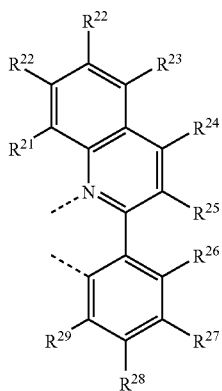

wherein $R^1$-$R^{29}$ represent hydrogen or independently selected substituents.

The ppy can be a 2-phenylpyridine group as represented by the following formula,

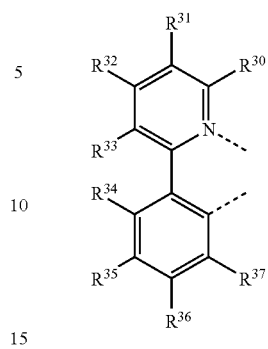

wherein $R^{30}$-$R^{37}$ represent hydrogen or independently selected substituents, provided one or more of $R^{30}$ and $R^{31}$, $R^{31}$ and $R^{32}$, $R^{32}$ and $R^{33}$, $R^{33}$ and $R^{34}$, $R^{34}$ and $R^{35}$, $R^{35}$ and $R^{36}$, as well as $R^{36}$ and $R^{37}$ may form a ring group. Conveniently, the ppy group can be chosen from the following or their derivatives:

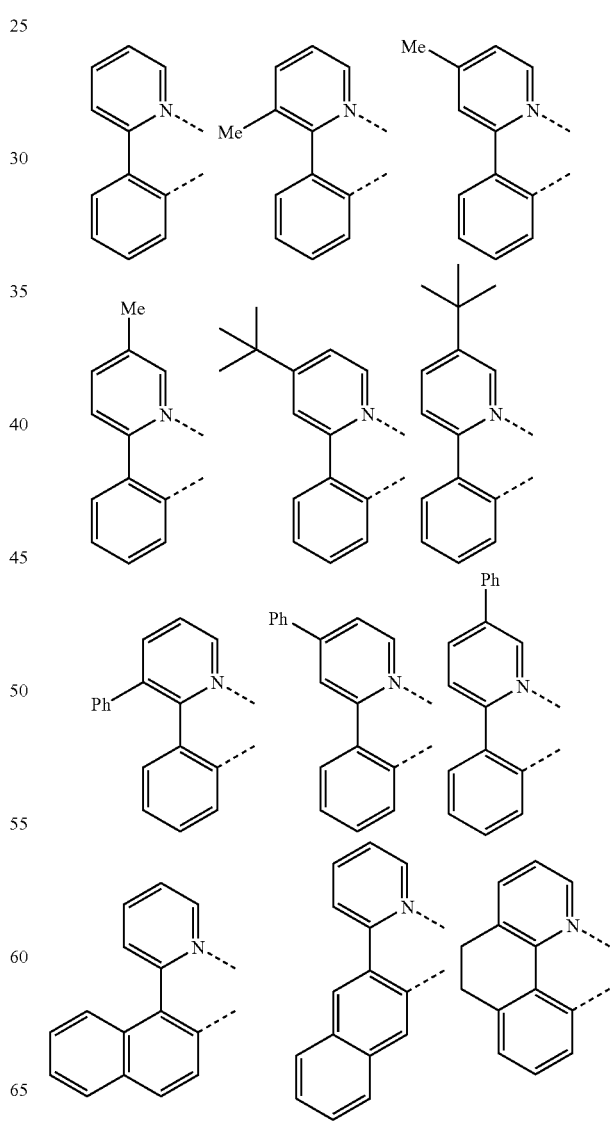

-continued

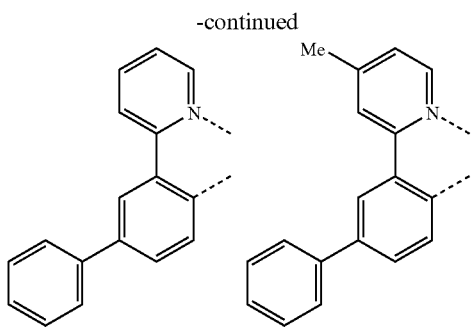

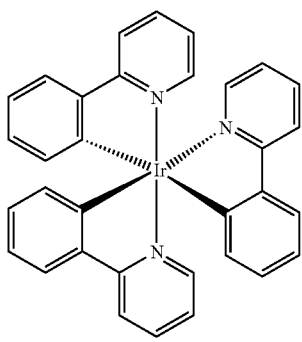

The precursors for the isomerization process, namely meridional tris-cyclometallated iridium complexes, can be prepared according to the procedure described in the prior art by reacting an organozinc complex of a desired organic ligand with a suitable halide-bridged di-nuclear bis-cyclometallated iridium complex (S. Huo, U.S. Pat. No. 6,835,835). They may also be prepared by other published methods (A. B. Tamayo, et al, *J. Am. Chem. Soc.* 2003, 125, 7377). Some representative meridional complexes are shown below,

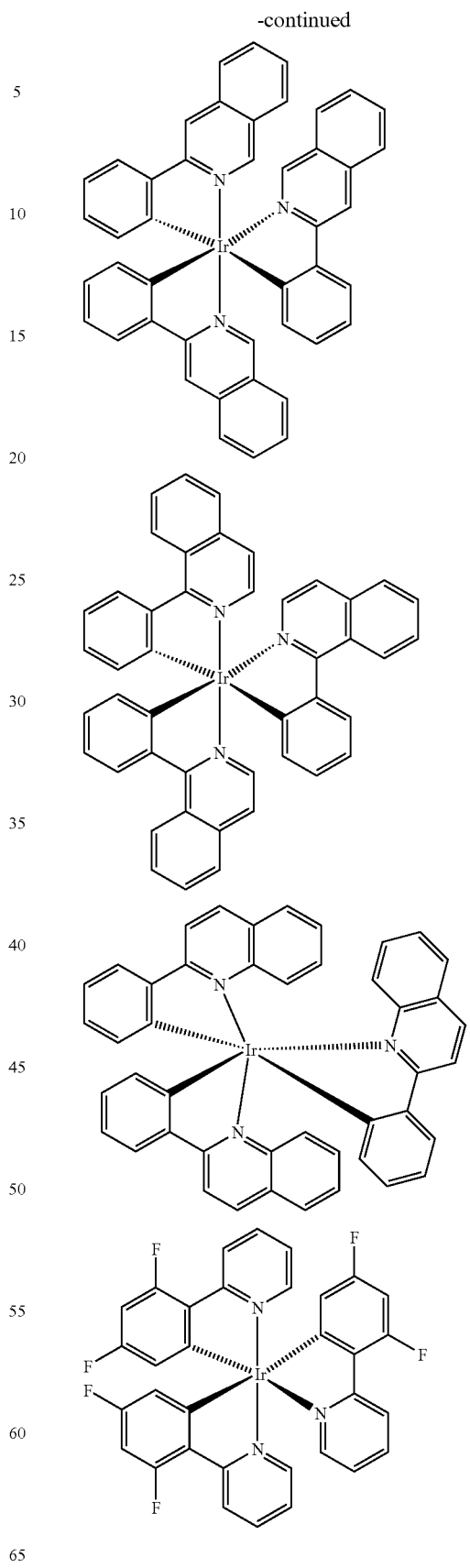

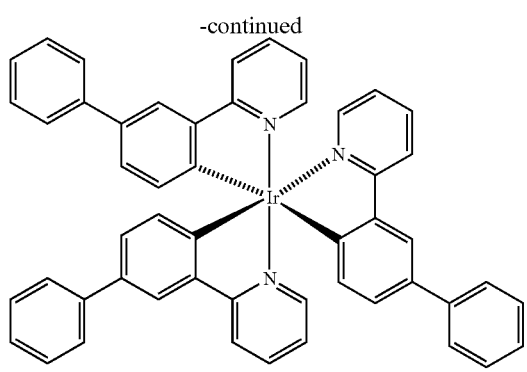
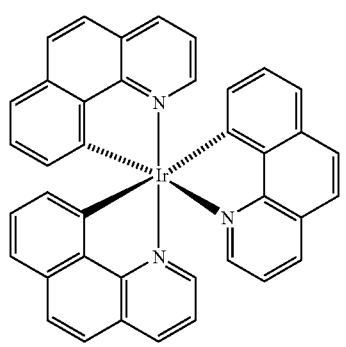
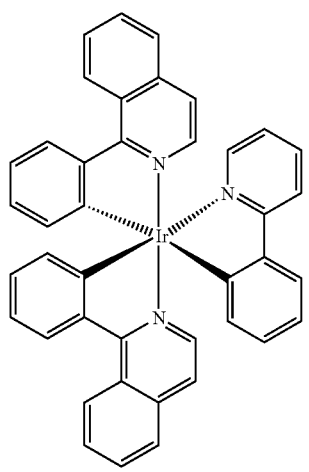
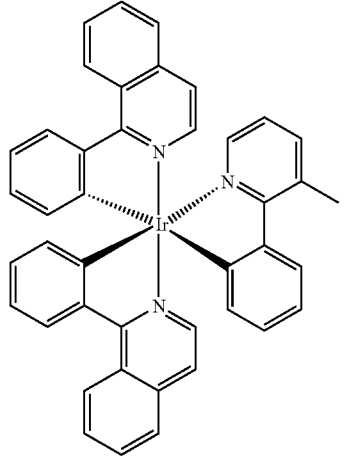
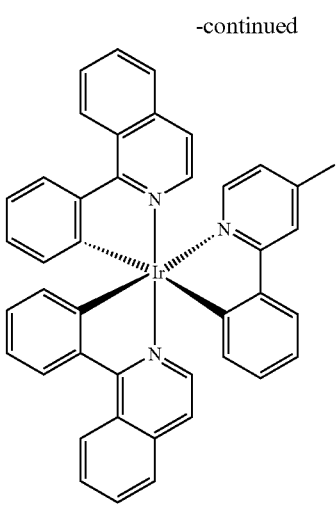
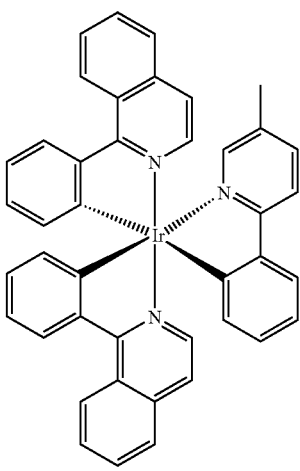
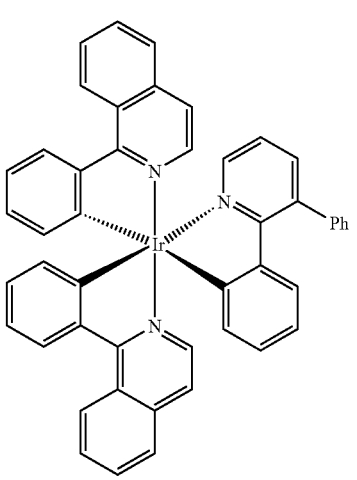

-continued
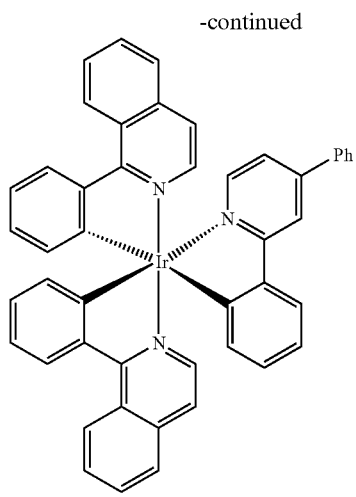
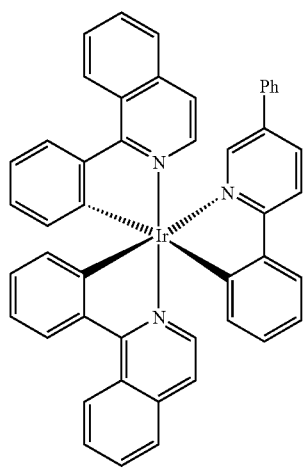
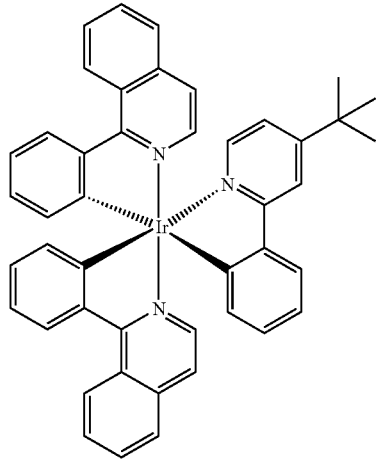
-continued
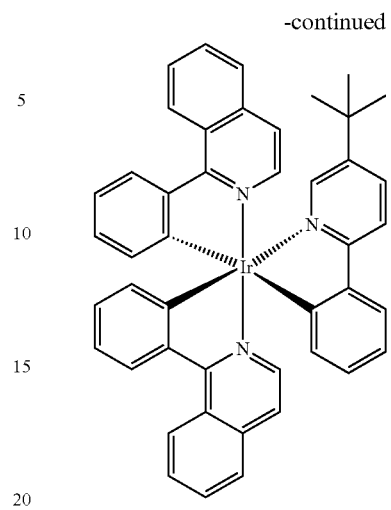
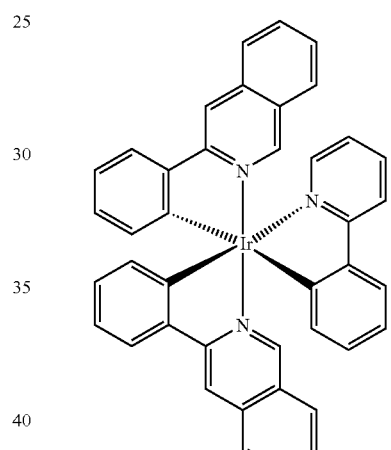
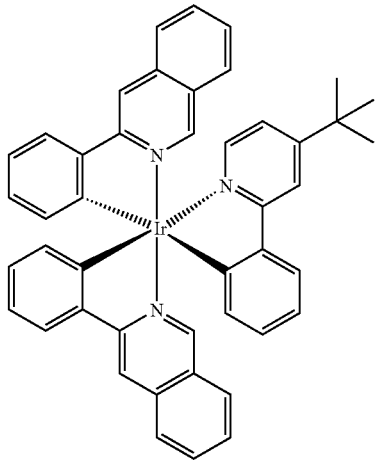

-continued

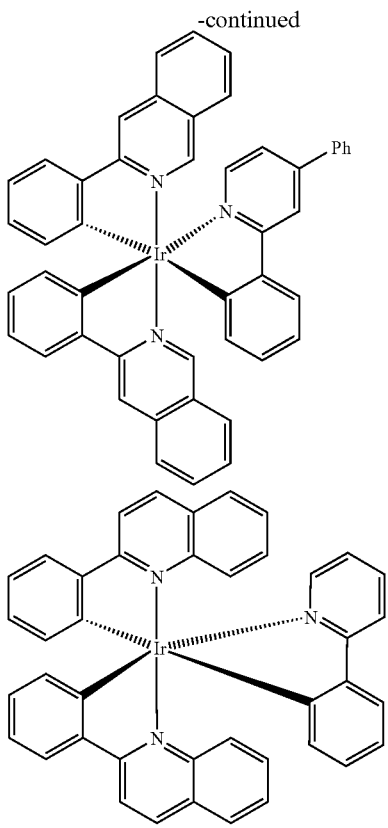

The isomerization reaction can be carried out by heating a composition containing meridional tris-cyclometallated Ir or Rh complex in an organic hydrocarbon solvent or halogenated hydrocarbon solvent. The hydrocarbon solvent is defined as an organic solvent that contains only carbon and hydrogen atoms and can be represented by general formula $C_nH_m$. The halogenated hydrocarbon solvent is defined as an organic solvent that contains only carbon, hydrogen, and halogen atoms and can be represented by the formula $C_nH_mX_1$ wherein X represent F, Cl, Br, or I. Compared with the solvent used in prior arts, such as glycerol and DMSO, a hydrocarbon solvent is "inert" to most chemical transformations, therefore, the use of a hydrocarbon solvent can avoid decompositions caused by the reactions occurred between the solvent and the starting material or product. More importantly, by using a hydrocarbon solvent, the ligand-scrambling side reactions in the case of heteroleptic tris-cyclometallated metal complexes can be suppressed. Such ligand scrambling has been a severe problem when using glycerol as the solvent for the isomerization of mer-Ir(1-piq)$_2$(ppy).

The hydrocarbon solvent can be a saturated alkane, an alkene, an alkyne, or a hydrocarbon compound containing one or more aromatic groups. The alkane can be a normal alkane, a branched alkane, or a cycloalkane. Desirably, the solvent is an alkane represented by the formula $C_nH_{2n+2}$ wherein the n represents a number selected from 13 to 17. Conveniently, the alkane is tridecane, tetradecane, pentadecane, or hexadecane. Further, the solvent can be an alkene. The alkene can be either linear or branched or cyclic. The alkene may contain more than one double bond. Conveniently, the alkene can be selected from 1-tridecene, 1-tetradecene, 1-pentadecene, and 1-hexadecene. Further, the solvent can be an alkyne.

The hydrocarbon solvent can be aromatic or contain an aromatic group. Suitably, the solvent can be substituted benzene wherein the substituent can be an alkyl, alkenyl, or alkynyl group and the number of substituents can be one or more. Conveniently, the solvent may be hexylbenzene, heptylbenzene, or octylbenzene.

The halogenated hydrocarbon solvent may contain one or more than one halogen atom. The halogen can be selected from F, Cl, Br, or I. Suitably, the halogen is selected from F or Cl. Conveniently, the halogenated solvent can be selected from 1-chlorooctane, 1-chlorononane, 1-chlorodecane, 1-chloroundecane, and 1-chlorododecane.

A mixture of two or more hydrocarbon solvents may be used in the isomerization process.

The temperature employed in the isomerization process should be sufficient for the isomerization to take place. A temperature of at least 150° C. is desirable. (Note: whether at or above atmospheric pressure, a temperature of at least 150° C. is needed.) The temperature can be elevated to 200 or 225° C. or higher to promote isomerization within a reasonable period of time. However, if the temperature is too high, decompositions of either the starting material or the product may be a problem. An optimal temperature may be substrate dependent and may be determined for a particular substrate. The isomerization reaction can be carried out by refluxing a mixture of a composition containing a meridional tris-cyclometallated iridium complex and an organic hydrocarbon solvent. In this case, a convenient solvent should have a boiling point that is sufficiently high for the isomerization of the meridional isomer to its facial isomer to take place at the boiling point. The boiling point of the solvent can be higher than the temperature required for the isomerization process. Conveniently, the boiling point of the solvent should be greater than 150° C. and is typically between 200 and 300° C. The isomerization process may also be carried out under pressure wherein the solvent with a lower boiling point may be used depending upon the pressure applied to the reaction system.

The formation of ligand-scrambling by-products in the isomerization of heteroleptic tris-cyclometallated iridium complexes is significantly suppressed using the process of the invention. The product can be purified by column chromatography and/or recrystallization to achieve high isomeric purity. Isomeric purity is defined as relative amount of the facial isomer to the total amount of both facial and meridional isomers. Further, the purity of the desired compound can be further improved through sublimation.

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy)propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino,p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl; octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

Synthesis

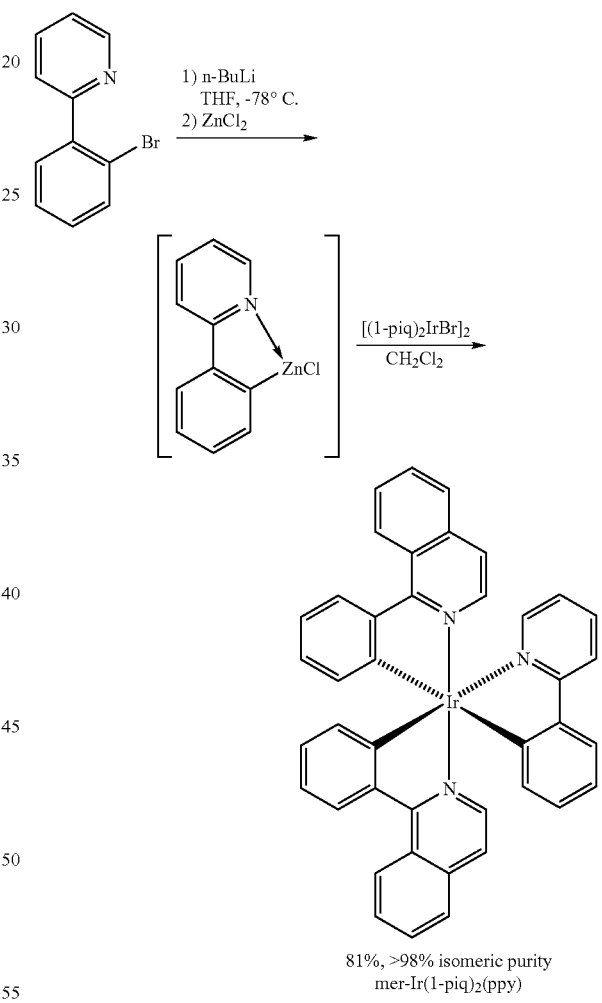

81%, >98% isomeric purity
mer-Ir(1-piq)₂(ppy)

Synthesis of meridional tris-cyclometallated iridium complex, mer-Ir(1-piq)₂(ppy): A solution of 2-(2-bromophenyl)pyridine (1.8 g, 7.5 mmol) in anhydrous THF (30 mL, Aldrich) was cooled to −78° C. with a dry ice-acetone bath. To this solution was added dropwise a solution of n-BuLi in hexanes (5.2 mL, 1.6 M, 8.3 mmol, Aldrich). The mixture was stirred at −78° C. for 30 min and a solution of ZnCl₂ in ether (7.5 mL, 1.0 M, 7.5 mmol, Aldrich) was added slowly via a syringe. The cooling bath was removed and the reaction mixture was warmed to about room temperature. The bromidebridged dimer [Ir(piq)$_2$Br]$_2$ (2.03 g, 1.5 mmol) was added to the reaction mixture in one portion. Anhydrous dichloromethane (30 mL) was added. After the mixture was refluxed for 6 hours, any remaining organozinc reagent was quenched with 5 mL of methanol. The mixture was poured into water (200 mL) and extracted with dichloromethane (3×100 mL). The combined organic layers were washed with water (2×100 mL) and brine (200 mL) and dried over MgSO$_4$. After filtration, the solvents were evaporated and the crude materials were dissolved in minimum amount of hot dichloromethane. Addition of methanol led to the precipitation of the product, which was collected by filtration, washed thoroughly with methanol and diethyl ether, and dried in air to yield yellow orange solids, meridional bis-(1-phenylisoquinoline-C$^2$,N)(phenylpyridinato-C$^2$,N)iridium(III), 1.85 g, 82%. The product can be further purified by recrystallization. The meridional configuration of the titled compound has been confirmed by X-ray crystal structure analysis.

Isomerization

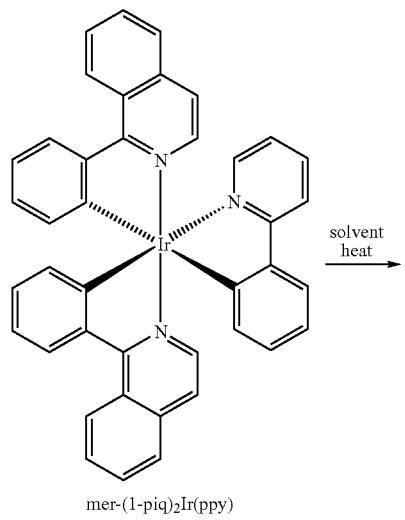

mer-(1-piq)$_2$Ir(ppy)

solvent
heat
→ fac-(1-piq)$_2$Ir(ppy)

EXAMPLE 1

Isomerization of meridional tris-cyclometallated iridium complex, mer-r(piq)$_2$(ppy): A dry flask was charged with mer-Ir(piq)$_2$(ppy) (200 mg, mer/fac ratio >99:1 by HPLC peak area) and anhydrous hexadecane (20 mL). The mixture was stirred under nitrogen atmosphere at ca. 250° C. for 3 hr. After cooling to room temperature, the mixture was diluted with heptane and the crude product was collected by filtration. The crude materials contained 93.9% (by HPLC peak area) fac-Ir(1-piq)$_2$(ppy), 4.3% mer-Ir(1-piq)$_2$(ppy), and ~1% of ligand scrambling by-products. The crude materials were dissolved in dichloromethane and filtered through a silica gel plug and washed with dichloromethane. The filtrate was concentrated and the product fac-Ir(1-piq)$_2$(ppy) was precipitated by addition of heptane, to yield 133 mg, 66%, >95% isomeric purity.

EXAMPLE 2

Isomerization of meridional tris-cyclometallated iridium complex, mer-Ir(piq)$_2$(ppy): A dry flask was charged with mer-Ir(piq)$_2$(ppy) (400 mg, mer/fac ratio >99:1 by HPLC peak area) and anhydrous tetradecane (20 mL). The mixture was refluxed under nitrogen atmosphere for 2 h. After cooling to room temperature, the mixture was diluted with heptane and filtered. The crude material contained 97% (by HPLC peak area) fac-Ir(1-piq)$_2$(ppy) and 3% mer-Ir(1-piq)$_2$(ppy). The crude materials was dissolved in dichloromethane and filtered through a silica gel plug and washed with dichloromethane. The filtrate was concentrated and the product fac-Ir(1-piq)$_2$(ppy) was precipitated by addition of methanol, 328 mg, 82%, >97% isomeric purity.

EXAMPLE 3

Isomerization of meridional tris-cyclometallated iridium complex, mer-Ir(piq)$_2$(ppy): A dry flask was charged with mer-Ir(piq)$_2$(ppy) (100 mg, mer/fac ratio >99:1 by HPLC peak area) and 1-tetradecene (tech. 92%, Aldrich, 10 mL). The mixture was refluxed under nitrogen atmosphere for 1.5 h. After cooling to room temperature, the mixture was diluted with heptane. The red solids were collected by filtration and washed with heptane and dried in air, to yield 78 mg, 78%, >99% isomeric purity.

EXAMPLE 4

Isomerization of meridional tris-cyclometallated iridium complex, mer-Ir(piq)$_2$(ppy): A dry flask was charged with mer-Ir(piq)$_2$(ppy) (100 mg, mer/fac ratio >99:1 by HPLC peak area) and anhydrous 1-heptylbenzene (10 mL). The mixture was refluxed under nitrogen atmosphere for 2 h. After cooling to room temperature, the mixture was diluted with heptane and filtered. The crude materials was dissolved in dichloromethane and filtered through a silica gel plug and washed with dichloromethane. The filtrate was concentrated and the product fac-Ir(1-piq)$_2$(ppy) was precipitated by addition of methanol, to yield 40 mg, 40%, >98% isomeric purity.

EXAMPLE 5

Isomerization of meridional tris-cyclometallated iridium complex, mer-Ir(piq)$_2$(ppy): A dry flask was charged with mer-Ir(piq)$_2$(ppy) (200 mg, mer/fac ratio >99:1 by HPLC peak area) and 1-chlorodecane (10 mL). The mixture was refluxed under nitrogen atmosphere for 3 h. After cooling to room temperature, the mixture was diluted with heptane and filtered. The crude materials was purified by flash chromatography on silica gel to provide pure fac-Ir(1-piq)$_2$(ppy) 70 mg, 35%, >99% isomeric purity.

COMPARATIVE EXAMPLE 1

Isomerization of meridional tris-cyclometallated iridium complex, mer-Ir(piq)$_2$(ppy): A dry flask was charged with mer-Ir(piq)$_2$(ppy) (100 mg, mer/fac ratio >99:1 by HPLC peak area) and anhydrous glycerol (10 mL). The mixture was refluxed under nitrogen atmosphere for two minutes. After cooling to room temperature, HPLC analysis of the reaction mixture indicated that most of the starting material was decomposed, producing free ligands ppy and 1-piq, along with a number of tris-cyclometallated Ir complexes including the desired product fac-Ir(1-piq)$_2$(ppy) as well as ligand scrambling by-products fac-Ir(ppy)$_3$, fac-Ir(1-piq)(ppy)$_2$, and fac-Ir(1-piq)$_3$ with ratio of 6:8:11:12 (by HPLC peak area).

COMPARATIVE EXAMPLE 2

Isomerization of meridional tris-cyclometallated iridium complex, mer-Ir(piq)$_2$(ppy): A dry flask was charged with mer-Ir(piq)$_2$(ppy) (100 mg, mer/fac ratio >99:1 by HPLC peak area) and anhydrous DMSO (10 mL). The mixture was refluxed under nitrogen atmosphere for 1 h. After cooling to room temperature, HPLC analysis of the reaction mixture indicated that most of the starting material decomposed, producing free ligands ppy and 1-piq, along with a number of other materials including the desired product that was present only as a minor component in the reaction mixture.

COMPARATIVE EXAMPLE 3

Isomerization of meridional tris-cyclometallated iridium complex, mer-Ir(piq)$_2$(ppy): A dry flask was charged with mer-Ir(piq)$_2$(ppy) (100 mg, mer/fac ratio >99:1 by HPLC peak area) and anhydrous 1-decanol (10 mL). The mixture was refluxed under nitrogen atmosphere for 2 h. After cooling to room temperature, HPLC analysis of the reaction mixture indicated that most of the starting material decomposed, producing largely free ligands ppy and 1-piq, along with a mixture of different tris-cyclometallated Ir complexes including the desired product fac-Ir(1-piq)$_2$(ppy) as a minor component.

COMPARATIVE EXAMPLE 4

Isomerization of meridional tris-cyclometallated iridium complex, mer-Ir(piq)$_2$(ppy): A dry flask was charged with mer-Ir(piq)$_2$(ppy) (100 mg, mer/fac ratio >99:1 by HPLC peak area) and di-octyl ether (10 mL). The mixture was stirred under nitrogen atmosphere at 200° C. for 12 h. After cooling to room temperature, HPLC analysis of the reaction mixture indicated that most of the starting material decomposed, producing largely free ligands ppy and 1-piq, along with a mixture of different compounds including the desired product fac-Ir(1-piq)$_2$(ppy).

It should be mentioned that the reaction conditions described in the examples are not optimized and one skilled in the field can readily optimize the reaction parameters for each individual reaction.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

The invention claimed is:

1. A process for forming a facial tris-cyclometallated iridium or rhodium complex isomer comprising heating composition containing (a) a meridional isomer of a tris-cyclometallated iridium or rhodium complex in (b) an organic hydrocarbon solvent, a halogenated hydrocarbon solvent, or a combination thereof, to a reaction temperature of least 150° C. for a time sufficient to form a product containing the facial tris-cyclometallated iridium or rhodium complex isomer in an increased ratio to meridional tris-cyclometallated iridium or rhodium complex isomer compared to the original composition.

2. The process of claim 1 wherein the tris-cyclometallated iridium complex is a homoleptic complex of formula (1):

$$ML_3 \qquad (1)$$

wherein:
M is the metal Ir or Rh; and
L is a monoanionic bidentate ligand that can be coordinated to M through a carbon and a heteroatom donor.

3. The process of claim 1 wherein the tris-cyclometallated iridium complex is a heteroleptic complex of formula (2):

$$M(L')_2L'' \qquad (2)$$

or formula (3):

$$ML'L''L''' \qquad (3)$$

wherein either formula (2) or (3):
M is the metal Ir or Rh; and
L', L'', and L''' are monoanionic bidentate ligands that can be coordinated to M through a carbon and a heteroatom donor.

4. The process of claim 3 wherein the heteroleptic tris-cyclometallated iridium complex contains two different ligands according to the heteroleptic complex of formula (2).

5. The process of claim 4 wherein at least one of the ligands is selected from the group consisting of a 1-phenylisoquinoline group, a 3-phenylisoquinoline group, and a 2-phenyiquinoline group.

6. The process of claim 4 wherein at least one of the ligands is a 1-phenylisoquinoline group represented by the formula:

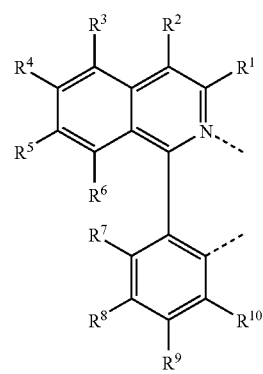

wherein $R^1$-$R^{10}$ each represent hydrogen or independently selected substituents.

7. The process of claim 4 wherein at least one of the ligands is a 3-phenylisoquinoline represented by the formula:

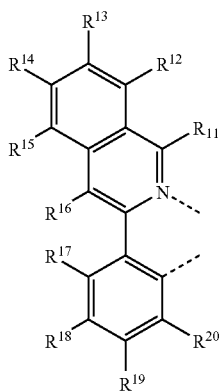

wherein $R^{11}$-$R^{20}$ each represent hydrogen or independently selected substituents.

8. The process of claim 4 wherein at least one of the ligands is a 2-phenylquinoline represented by the formula:

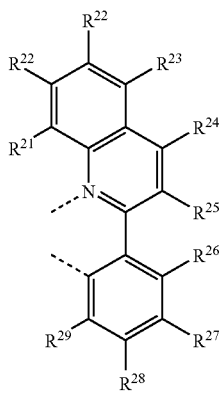

wherein $R^{21}$-$R^{29}$ each represent hydrogen or independently selected substituents.

9. The process of claim 4 wherein two of the ligands are 1-phenylisoquinoline groups and the other is a phenylpyridine group.

10. The process of claim 9 wherein the phenylpyridine ligand group is one selected from the substituted or unsubstituted forms of the following groups:

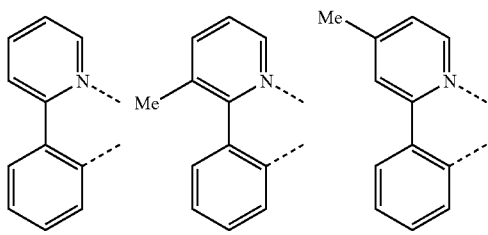

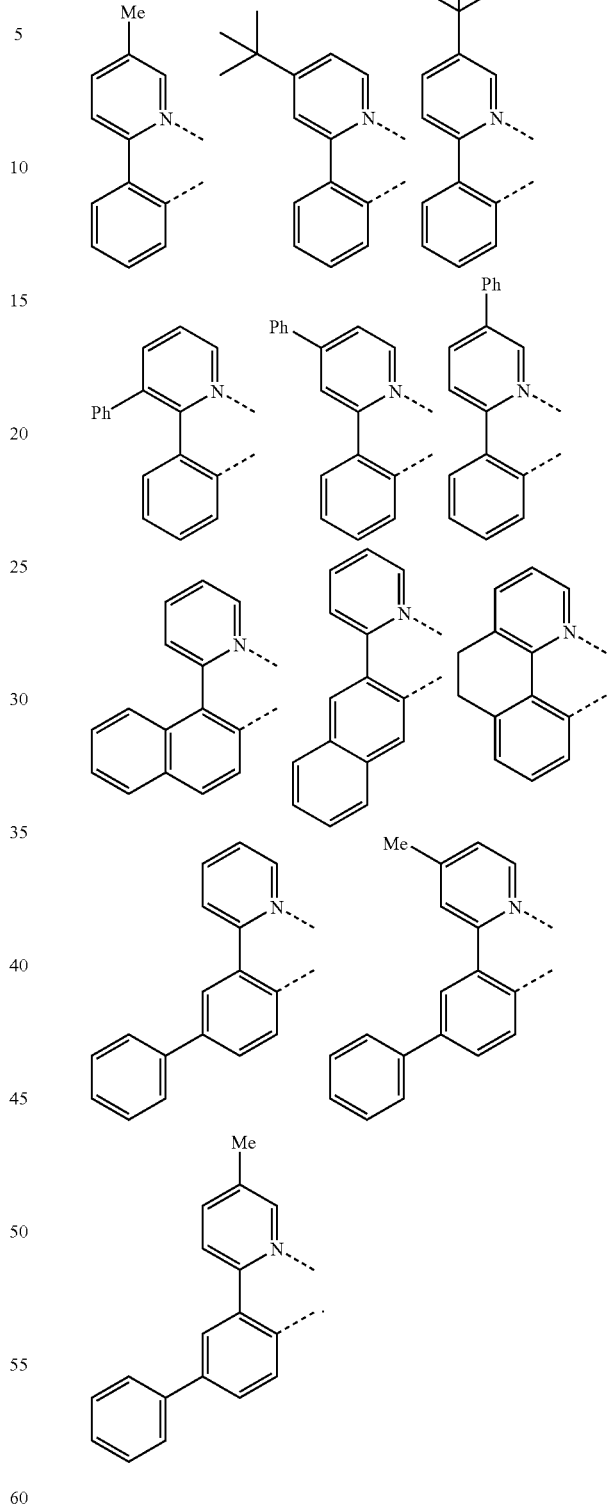

11. The process of claim 1 wherein the solvent comprises an alkane hydrocarbon.

12. The process of claim 11 wherein the alkane is a cycloalkane.

13. The process of claim 11 wherein the alkane contains from 13 to 17 carbon atoms.

14. The process of claim 1 wherein the solvent comprises an alkene hydrocarbon.

15. The process of claim 14 wherein the alkene is selected from 1-tetradecene, 1-pentadecene, and 1-hexadecene.

16. The process of claim 1 wherein the hydrocarbon solvent contains an aromatic group.

17. The process of claim 16 wherein the solvent is a substituted benzene wherein the substituent is an alkyl, alkenyl, or alkynyl group.

18. The process of claim 17 wherein the substituted benzene is selected from the group consisting of hexylbenzene, heptylbenzene, and octylbenzene.

19. The process of claim 1 wherein the solvent comprises a halogenated hydrocarbon solvent.

20. The process of claim 19 wherein the halogenated hydrocarbon solvent is selected from the group consisting of 1-chlorooctane, 1-chlorononane, 1-chlorodecane, 1-chloroundecane, and 1-chlorododecane.

21. The process of claim 1 wherein the reaction temperature is at least 200° C.

22. The process of claim 1 wherein the reaction temperature is at least 225° C.

* * * * *

UNITED STATES PATENT AND TRADEMARK OFFICE
CERTIFICATE OF CORRECTION

| | | |
|---|---|---|
| PATENT NO. | : 7,517,984 B2 | Page 1 of 1 |
| APPLICATION NO. | : 11/240288 | |
| DATED | : April 14, 2009 | |
| INVENTOR(S) | : Shouquan Huo | |

It is certified that error appears in the above-identified patent and that said Letters Patent is hereby corrected as shown below:

Title Page, Col. 2, Line 6 (Other Publications)  Delete "Tris-Cyclometalated" and insert --Tris-Cyclometallated--, therefor.

Title Page, Col. 2, Line 9 (Other Publications)  Delete "$(C_2N)_3$" and insert --$(C,N)_3$--, therefor.

Column 20, Lines 43-44  In Claim 5, delete "2-phenyiquinoline" and insert --2-phenylquinoline--, therefor.

Signed and Sealed this

Twenty-sixth Day of January, 2010

David J. Kappos
*Director of the United States Patent and Trademark Office*